United States Patent
Wallenstein et al.

(10) Patent No.: US 10,426,534 B2
(45) Date of Patent: Oct. 1, 2019

(54) SEMI-CONSTRAINED BONE SCREW AND INSERTION INSTRUMENT

(71) Applicant: K2M, Inc., Leesburg, VA (US)

(72) Inventors: Todd Wallenstein, Ashburn, VA (US); Megan Carnes, Leesburg, VA (US); John Donohoe, Sterling, VA (US)

(73) Assignee: K2M, Inc., Leesburg, VA (US)

( * ) Notice: Subject to any disclaimer, the term of this patent is extended or adjusted under 35 U.S.C. 154(b) by 75 days.

(21) Appl. No.: 15/332,225

(22) Filed: Oct. 24, 2016

(65) Prior Publication Data

US 2017/0112555 A1 Apr. 27, 2017

Related U.S. Application Data

(60) Provisional application No. 62/245,337, filed on Oct. 23, 2015.

(51) Int. Cl.
| | |
|---|---|
| *A61B 17/86* | (2006.01) |
| *A61B 17/70* | (2006.01) |
| *A61B 17/88* | (2006.01) |
| A61B 17/80 | (2006.01) |
| A61B 17/56 | (2006.01) |

(52) U.S. Cl.
CPC ...... *A61B 17/8605* (2013.01); *A61B 17/7082* (2013.01); *A61B 17/8615* (2013.01); *A61B 17/8625* (2013.01); *A61B 17/8635* (2013.01); *A61B 17/8685* (2013.01); *A61B 17/888* (2013.01); *A61B 17/808* (2013.01); *A61B 2017/564* (2013.01)

(58) Field of Classification Search
CPC . A61B 17/8052; A61B 17/8057; A61B 17/84; A61B 17/86; A61B 17/8605; A61B 17/861; A61B 17/8615; A61B 17/864; A61B 17/8685; A61B 17/844; A61B 17/7233; A61B 17/7258; A61B 17/7266; A61B 17/7275; A61B 2017/8655
See application file for complete search history.

(56) References Cited

U.S. PATENT DOCUMENTS

| | | |
|---|---|---|
| 8,388,660 B1 | 3/2013 | Abdou |
| 8,439,977 B2 | 5/2013 | Kostuik et al. |
| 8,449,585 B2 | 5/2013 | Wallenstein et al. |

(Continued)

OTHER PUBLICATIONS

European Search Report in corresponding Application No. 16195240, dated Mar. 31, 2017, 9 pages.

*Primary Examiner* — Lynnsy M Summitt
(74) *Attorney, Agent, or Firm* — Lerner, David, Littenberg, Krumholz & Mentlik, LLP (57) ABSTRACT

A bone screw for attaching a spinal prosthetic or bone plate to bone includes a tubular body having open proximal and distal ends. The open proximal and distal ends define a passageway therethrough. A shaft is insertable into the passageway and includes a distal tip that extends beyond the open distal end. The shaft is insertable through a lumen of a head of the bone screw. A gap is defined between a distal surface of the head and a proximal end of the tubular body. The shaft is rotationally fixed with the tubular body and the head. The head is repositionable with respect to the shaft such that an acute angle is defined between the head and a longitudinal axis of the shaft.

22 Claims, 5 Drawing Sheets

(56) References Cited

U.S. PATENT DOCUMENTS

| | | | |
|---|---|---|---|
| 8,529,611 B2* | 9/2013 | Champagne | A61B 17/7225 606/301 |
| 9,861,415 B2* | 1/2018 | Biedermann | A61B 17/8685 |
| 2002/0198527 A1 | 12/2002 | Muckter | |
| 2004/0147929 A1* | 7/2004 | Biedermann | A61B 17/7001 606/266 |
| 2004/0172031 A1* | 9/2004 | Rubecamp | A61B 17/8685 606/309 |
| 2005/0055026 A1* | 3/2005 | Biedermann | A61B 17/1659 606/278 |
| 2008/0132957 A1* | 6/2008 | Matthis | A61B 17/7032 606/301 |
| 2009/0030457 A1* | 1/2009 | Janowski | A61B 17/7032 606/246 |
| 2009/0281580 A1 | 11/2009 | Emannuel | |
| 2011/0106172 A1* | 5/2011 | Wallenstein | A61B 17/8685 606/286 |
| 2012/0215264 A1* | 8/2012 | Lee | A61B 17/7037 606/305 |
| 2012/0271423 A1* | 10/2012 | Wallenstein | A61B 17/8685 623/17.16 |
| 2013/0190817 A1* | 7/2013 | Bouduban | A61B 17/0401 606/232 |
| 2013/0190831 A1* | 7/2013 | Ek | A61F 2/4225 606/315 |
| 2013/0245697 A1* | 9/2013 | Hulliger | A61B 17/84 606/281 |
| 2013/0338722 A1* | 12/2013 | Yalizis | A61B 17/68 606/312 |
| 2014/0005731 A1* | 1/2014 | Biedermann | A61B 17/686 606/328 |
| 2014/0142639 A1* | 5/2014 | Vennard | A61B 17/8685 606/291 |
| 2014/0172027 A1* | 6/2014 | Biedermann | A61B 17/8625 606/326 |
| 2014/0188180 A1* | 7/2014 | Biedermann | A61B 17/8625 606/328 |
| 2014/0207195 A1* | 7/2014 | Appenzeller | A61B 17/68 606/304 |
| 2015/0105830 A1* | 4/2015 | Biedermann | A61B 17/8685 606/317 |
| 2015/0250516 A1 | 9/2015 | Vennard et al. | |
| 2015/0257807 A1* | 9/2015 | Strnad | A61B 17/8615 606/308 |

* cited by examiner

SEMI-CONSTRAINED BONE SCREW AND INSERTION INSTRUMENT

CROSS-REFERENCE TO RELATED APPLICATIONS

The present application claims the benefit of, and priority, to U.S. Provisional Patent Application Ser. No. 62/245,337, filed on Oct. 23, 2015, the entire contents of which are incorporated herein by reference.

BACKGROUND

1. Technical Field

The present disclosure relates to a bone screw and, more particularly, to a semi-constrained bone screw and insertion instrument for use with a surgical implant.

2. Background of the Technology

The human spinal column is a highly complex structure. It includes twenty-four discrete bones, known as vertebrae, coupled sequentially to one another to house and protect critical elements of the nervous system. In between adjacent vertebrae is a disc. Each disc functions as a shock absorber, absorbing the impact of the body's activities and distributing pressure under compressive loads. Additionally, each disc forms a fibro-cartilaginous joint between adjacent vertebrae, allowing movement of the vertebrae and acting as a ligament to hold the vertebrae together.

For many reasons, such as aging and trauma, the discs may begin to deteriorate and weaken, potentially resulting in chronic pain, degenerative disc disease, or even tearing of the disc. Ultimately, the disc may deteriorate or weaken to the point of herniation, in which the inner portions of the disc protrude through the tear. A herniated disc may press against, or pinch, the spinal nerves, thereby causing radiating pain, numbness, tingling, and/or diminished strength or range of motion. The surgical removal of a diseased disc is a common procedure in current medical practice. Spinal fusion procedures involve removing a damaged disc and replacing it with an artificial disc, such as a bone graft or bone graft substitute. To keep the artificial disc and the vertebrae fixed in place while bone healing occurs, an external fixation device, such as a bone plate, is used. Bone plates are secured to the vertebrae using bone screws, which typically require drilling holes into the vertebrae.

A common problem associated with the use of such a bone plate or spinal prosthetic is the tendency of the bone screws to "back out" or pull away or otherwise withdraw from the bone into which they are mounted. This problem occurs, primarily, due to the normal torsional and bending motions of the body and spine. As the screws become loose and pull away or withdraw from the bone, the heads of the screws can rise above the surface of the bone plate or spinal prosthetic, which results in pain and discomfort for the patient or possibly the separation of the bone plate from one or more vertebrae.

SUMMARY

The present disclosure relates to bone screws configured for use with a spinal prosthetic implant or bone plate. The bone screw includes a tubular body having open proximal and distal ends defining a passageway therethrough. A helical thread circumscribes an outer surface of the tubular body. The bone screw includes a head having threading thereon and a lumen extending therethrough. A shaft is insertable through the lumen and the passageway. The shaft couples the head to the tubular body such that a gap is defined between a distal surface of the head and the open proximal end of the tubular body. The head is repositionable with respect to the tubular body.

The head may be configured to define an acute angle with respect to a longitudinal axis of the shaft.

The passageway may define a proximal cavity having a first diameter and a distal cavity having a second diameter less than the first diameter.

The shaft may have a proximal body portion and a distal body portion. The proximal body portion may be configured for insertion into the proximal cavity and the distal body portion may be configured for insertion into the distal cavity.

The proximal body portion may include a hexagonal configuration that is complementary to a hexagonal configuration of the proximal cavity thereby inhibiting relative rotation between the shaft and the tubular body.

The shaft may include a neck portion distal of the distal portion and a tip located distally of the neck portion. The open distal end of the tubular body may be sized to receive the neck portion. The tip may be pointed for engaging bone.

The neck portion may have an outer diameter less than an outer diameter of the distal body portion and the tip such that the neck portion is retained in a channel of the open distal end thereby inhibiting relative axial movement between the shaft and the tubular body.

The lumen of the head may be configured for releasably engaging a driving tool. The shaft of the bone screw may include a flared portion at a proximal end wherein the flared portion includes fingers. A distal portion of the driving tool may be attachable to the fingers of the flared portion of the shaft.

The present disclosure also relates to a system for securing spinal fixation devices. The system includes a bone screw having a tubular body with open proximal and distal ends defining a passageway therethrough. A helical thread circumscribes an outer surface of the tubular body. The bone screw also includes a head having threading thereon with a lumen extending through the head. A shaft is insertable through the lumen of the head and the passageway of the tubular body, the shaft coupling the head to the tubular body such that a gap is defined between a distal surface of the head and the open proximal end of the tubular body. The head is repositionable with respect to the tubular body. The system also includes a driving tool with an elongate shaft having a proximal portion and a distal portion. A handle extends from the proximal portion of the elongate shaft and a driving bit extends from the distal portion of the elongate shaft. The driving bit has a hexagonal configuration on an outer surface thereof and defines a cavity therein.

The driving bit may have a diameter that is less than a diameter of the elongate shaft.

The hexagonal configuration of the driving bit may be complementary to a hexagonal configuration of the lumen of the head of the bone screw to enable selective rotation of the bone screw.

The shaft of the bone screw may include a flared portion at a proximal end thereof. The flared portion may include fingers that are selectively attachable with the cavity of the driving bit.

The cavity of the driving bit may define a groove therein. The fingers of the flared portion may be selectively receivable in the groove to axially fix the bone screw to the driving tool.

A method of performing a spinal procedure is also disclosed. The method includes attaching a bone screw to a driving tool. The bone screw includes a tubular body having open proximal and distal ends defining a passageway therethrough and a helical thread circumscribing an outer surface of the tubular body. The bone screw also includes a head having threading thereon and the head having a lumen extending therethrough. A shaft of the bone screw is insertable through the lumen of the head and the passageway of the tubular body. The shaft couples the head to the tubular body such that a gap is defined between a distal surface of the head and the open proximal end of the tubular body. The head is repositionable with respect to the tubular body. The method also includes rotating the driving tool and fastening the bone screw into a bony structure.

The method of attaching the bone screw to the driving tool may also include the driving tool having an elongate shaft with a proximal portion and a distal portion. A driving bit may extend from the distal portion of the elongate shaft. The driving bit may have a hexagonal configuration on an outer surface thereof and may define a cavity therein.

The method may further include inserting fingers of a flared portion of the shaft into a groove defined in the cavity of the driving bit. The method may also include advancing the driving tool distally until the fingers are selectively and releasably coupled in the groove to axially fix the bone screw to the driving tool.

The method may further include positioning the head of the bone screw to define an acute angle with respect to a longitudinal axis of the shaft of the bone screw.

BRIEF DESCRIPTION OF THE DRAWINGS

Embodiments of the presently disclosed semi-constrained bone screw are described herein with reference to the accompanying drawings, wherein.

DETAILED DESCRIPTION OF THE EMBODIMENTS

Various embodiments of the presently disclosed semi-constrained bone screw will now be described in detail with reference to the drawings, wherein like reference numerals identify similar or identical elements. In the drawings and in the description that follows, the term "distal," as is conventional, will refer to that portion of the instrument, apparatus, device or component thereof which is farther from the user while the term "proximal," will refer to that portion of the instrument, apparatus, device or component thereof which is closer to the user. In the following description, well-known functions or constructions are not described in detail to avoid obscuring the present disclosure in unnecessary detail.

Figure 1:
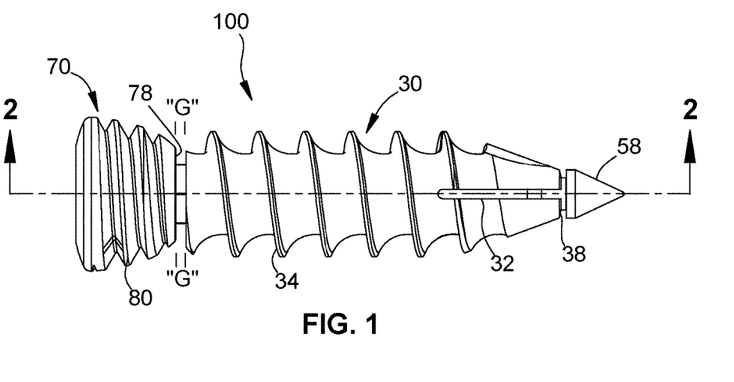
FIG. 1 is a side view of a semi-constrained bone screw in accordance with the present disclosure.
Figure 2:
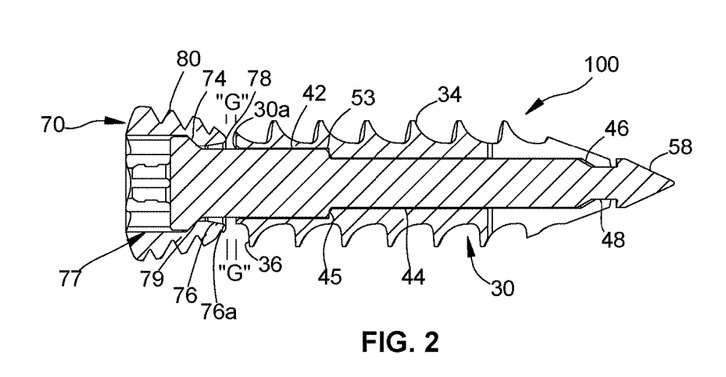
FIG. 2 is a side cross-sectional view of the semi-constrained bone screw of FIG. 1 taken along section line 2-2.

With initial reference to FIGS. 1 and 2, an embodiment of a semi-constrained bone screw or bone screw is illustrated and generally designated as reference numeral 100. Bone screw 100 includes a tubular body 30, a shaft 50 insertable into and through the tubular body 30, and a head 70. Bone screw 100 is usable with a driving tool 150 (FIGS. 8-11) as will be described in more detail hereinbelow. Examples of a suitable bone screw and driving tool are disclosed in U.S. Patent Application Publication No. 2015/0257807 filed on Ma. 12, 2015, the entire contents of which is hereby incorporated by reference herein. It is contemplated that one or more of the tubular body 30, the shaft 50, and the head 70 may be fabricated using additive manufacturing techniques as an alternative to traditional fabrication techniques. The tubular body 30 of the bone screw 100 has a helical thread 34 circumscribing an outer surface thereof. A distal region of the tubular body 30 includes one or more slits 32. Each slit 32 extends from an open distal end 38 of the tubular body 30 proximally for only a portion of the length of the tubular body 30. The distal region of the tubular body 30 is expandable from an initial outer diameter as shown in FIG. 1 to an increased outer diameter (not shown) that allows the shaft 50 of the bone screw 100 to be inserted through the open distal end 38 of the tubular body 30 as will be explained hereinbelow in further detail.

The head 70 of the bone screw 100 has threading 80 disposed on an outer surface thereof. The helical thread 34 of the tubular body 30 is configured for engaging bone. The threading 80 disposed on the head 70 is configured for engaging an aperture of a spinal prosthetic or bone plate (not shown) and may be configured for engaging bone. A gap "G" is defined between a distal surface 78 of the head 70 and a proximal surface 36 of the tubular body 30. The gap "G," in combination with the configuration of the head 70 and shaft 50 of the bone screw 100, allows the head 70 to be repositioned with respect to a longitudinal axis of the bone screw 100 such that the head 70 may define a plurality of acute angles "α" (FIGS. 5 and 6) with respect to the longitudinal axis of the bone screw 100.

As shown in FIG. 2, the tubular body 30 defines a proximal cavity 42, located adjacent to an open proximal end 30a of the tubular body 30, and a distal cavity 44 that extends distally from the proximal cavity 42 of the tubular body 30. The proximal cavity 42 of the tubular body 30 has an inner diameter that is greater than an inner diameter of the distal cavity 44 of the tubular body 30, thereby defining a shoulder 45 at the junction of the proximal and distal cavities 42, 44. A distal end 46 of the distal cavity 44 tapers inwardly. A channel 48 of the tubular body 30 connects the distal cavity 44 with the open distal end 38 of the tubular body 30. The channel 48 has an inner diameter comparable to the diameter of the open distal end 38 of the tubular body 30.

Figure 3:
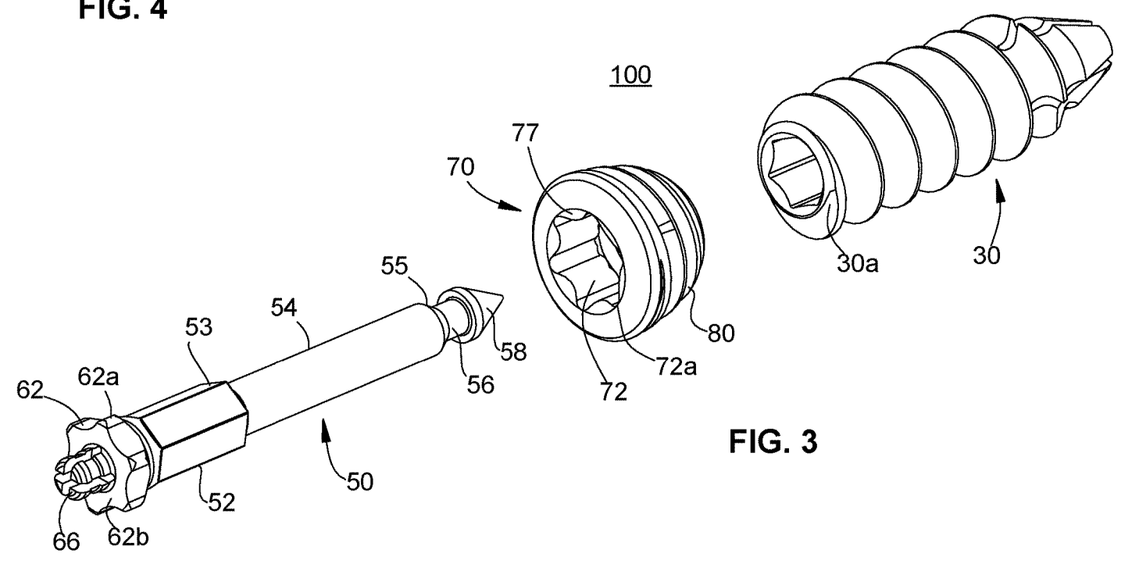
FIG. 3 is an exploded perspective view, with parts separated, of the semi-constrained bone screw of FIG. 1.

With reference to FIG. 3, the shaft 50 of the bone screw 100 has a distal tip 58 that may be pointed for engaging bone. A neck portion 56 of the shaft 50 is adjacent to the distal tip 58 of the shaft 50 and has an outer diameter less than a maximum outer diameter of the distal tip 58. The shaft 50 also includes a distal body portion 54 extending proximally from the neck portion 56. The distal body portion 54 has an outer diameter that is greater than the outer diameter of the neck portion 56 and substantially similar to the maximum outer diameter of the distal tip 58. Additionally, a distal end or tapered junction 55 of the distal body portion 54 is tapered inwardly to correspond to the inward taper of the distal end 46 of the distal cavity 44. In this configuration, the neck portion 56 is maintained in the channel 48 of the tubular body 30, thereby inhibiting relative axial movement between the tubular body 30 and the shaft 50. The distal body portion 54 of the shaft 50 is adjacent to a proximal body portion 52 of the shaft 50, the proximal body portion 52 having an outer diameter greater than the outer diameter of the distal body portion 54. As such, a distal end surface 53 of the proximal body portion 52 abuts the shoulder 45 of the tubular body 30 at the junction of the proximal and distal cavities 42, 44 of the tubular body 30. This arrangement limits the distal travel of the shaft 50 with respect to the tubular body 30. In combination with the neck portion 56 located in the channel 48 of the tubular body 30, the relative positions of the shaft 50 and tubular body 30 of the bone screw 100 are fixed upon assembly. Extending proximally from the proximal portion 52 is a flared portion 62. The flared portion 62 has an outwardly extending flare with a maximum outer diameter greater than that of the proximal body portion 52.

The head 70 of the bone screw 100 has a lumen 72 extending therethrough. A proximal opening 77 of the lumen 72 has a greater diameter than a distal opening 76 of the lumen 72. A distal region 74 of the lumen 72 tapers inwardly to a reduced diameter section 79 that has a diameter less than the maximum diameter of the flared portion 62 of the shaft 50, but greater than the outer diameter of the proximal body portion 52 of the shaft 50. This arrangement allows the shaft 50 to be inserted through the lumen 72 in only one orientation (i.e., distal tip 58 of the shaft 50 first) and acts as a stop to maintain the flared portion 62 of the shaft 50 within the lumen 72. The distal opening 76 has a taper 76a that extends generally outwards and increases the angular range of the head 70 of the bone screw 100 relative to the shaft 50 of the bone screw 100.

Figure 4:
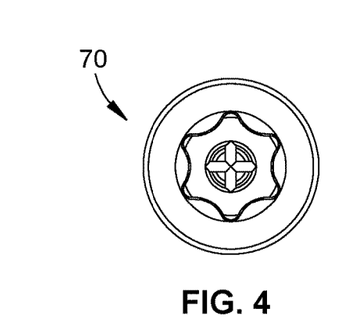
FIG. 4 is an end view of the semi-constrained bone screw of FIG. 1.

Referring now to FIGS. 3 and 4, the proximal body portion 52 of the shaft 50 has a hexagonal configuration that is complementary to a hexagonal configuration of the proximal cavity 42 of the tubular body 30. Although shown as a hexagonal shape, other geometric shapes (e.g., triangular, rectangular, etc.) are contemplated with the proximal body portion 52 and the proximal cavity 42 having complementary shapes to inhibit relative rotation between the two components. The lumen 72 of the head 70 has an inner surface 72a with a hexolobular arrangement for engaging driving tool 150 (FIGS. 8-11), as will be described below. Other arrangements (e.g., Phillips head, star head, Allen head, etc.) are also contemplated. Likewise, the flared portion 62 of the shaft 50 has a complementary hexolobular configuration 62a. When the flared portion 62 is positioned in the lumen 72 of the head 70, the head 70 and shaft 50 of the bone screw 100 are rotationally fixed. Thus, rotation of one of the head 70 and shaft 50 of the bone screw 100 results in corresponding rotation of the other. The distal body portion 54 and the neck portion 56 of the shaft 50 are generally circular and are separated by a tapered junction 55. The tubular body 30 portion includes flutes 31 at the distal end thereof. The flutes 31 may enable the tubular body 30 to be a self-starting type screw or a self-tapping type screw. In embodiments, tubular body 30 may have any suitable diameter for engaging bone, such as 4.0 mm to 4.5 mm.

A plurality of fingers 66 of the shaft 50 extend proximally from a top surface 62b of the flared portion 62 of the shaft 50. Shaft 50 is illustrated as having four fingers 66, but it is contemplated that the flared portion 62 may have more than four fingers 66 or fewer than four fingers 66. Fingers 66 are flexibly attached to the top surface 62b of flared portion 62 and are configured to flex towards and away from a central longitudinal axis of the shaft 50. The fingers 66, in an initial position, are biased away (e.g., outwardly) from the central longitudinal axis and are configured for releasably engaging a distal portion of the driving tool 150 (FIG. 11) as will be discussed in detail hereinbelow.

Bone screw 100 is assembled by coupling the tubular body 30, the shaft 50, and the head 70 of the bone screw 100 together. Initially, the distal tip 58 of the shaft 50 is inserted into the proximal opening 77 of head 70 and through the lumen 72 of the head 70. With the shaft 50 extending through the head 70 of the bone screw 100, the distal tip 58 is subsequently inserted into the open proximal end 30a of the tubular body 30 until the distal tip 58 exits the open distal end 38 of the tubular body 30. The diameter of the distal tip 58 is greater than the diameter of the channel 48 of the tubular body 30. Thus, as the distal tip 58 moves through slits 32 of the tubular body 30, slits 32 expand, thereby allowing distal translation of the shaft 50 through the tubular body 30 of the bone screw 100.

Once the distal tip 58 of the shaft 50 exits the open distal end 38 of the tubular body 30, the slits 32 decompress from their expanded position and return tubular body 30 to its initial diameter and capture the neck portion 56 of the shaft 50 in the channel 48 of the tubular body 30. As assembled, the distal end surface 53 of the proximal body portion 52 of the shaft 50 abuts the shoulder 45 of the tubular body 30 to limit relative distal movement between the tubular body 30 and the shaft 50, while the neck portion 56 of the shaft 50 is situated in the channel 48 of the tubular body 30 to limit relative proximal movement between the tubular body 30 and the shaft 50 and to axially fix the position of the shaft 50 relative to the tubular body 30 such that bone screw 100 is ready for use.

With the bone screw 100 assembled (FIG. 1), the bone screw 100 is insertable into an opening in bone (e.g., drilled or tapped) using driving tool 150 that engages the hexolobular inner surface 72a of the lumen 72 of the head 70. As the head 70 of the bone screw 100 rotates, the flared portion 62 of the shaft 50 rotates, thereby transferring the rotational movement of the driving tool 150 through the head 70, the shaft 50, and the tubular body 30 of the bone screw 100 such that the bone screw 100 can be translated into or out of the opening in bone.

Figure 5:
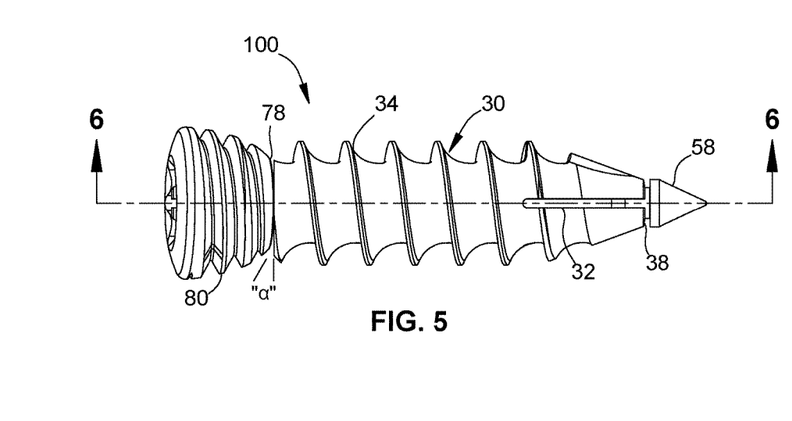
FIG. 5 is a side view of the semi-constrained bone screw of FIG. 1 with the head at an angle with respect to the longitudinal axis of the semi-constrained bone screw.
Figure 6:
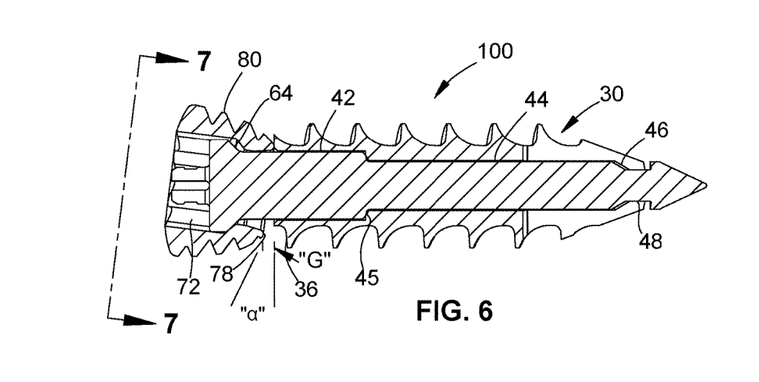
FIG. 6 is a side cross-sectional view of the semi-constrained bone screw of FIG. 5 taken along section line 6-6.
Figure 7:
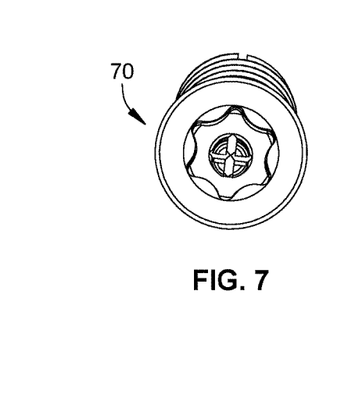
FIG. 7 is an end view of the semi-constrained bone screw of FIG. 6 viewed along section line 7-7.
Figure 8:
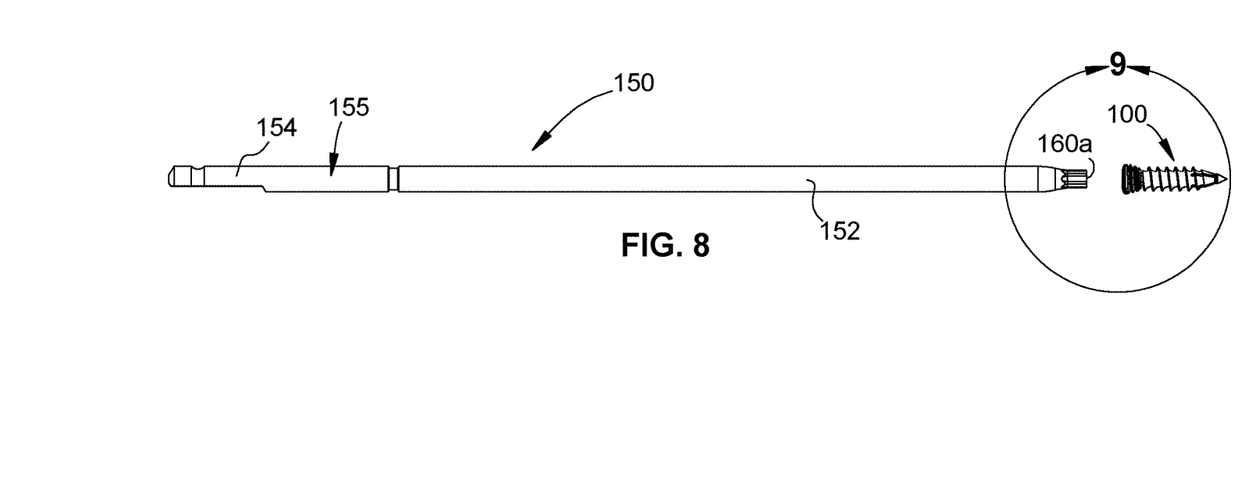
FIG. 8 is side view of a driving tool and the semi-constrained bone screw of FIG. 1.
Figure 9:
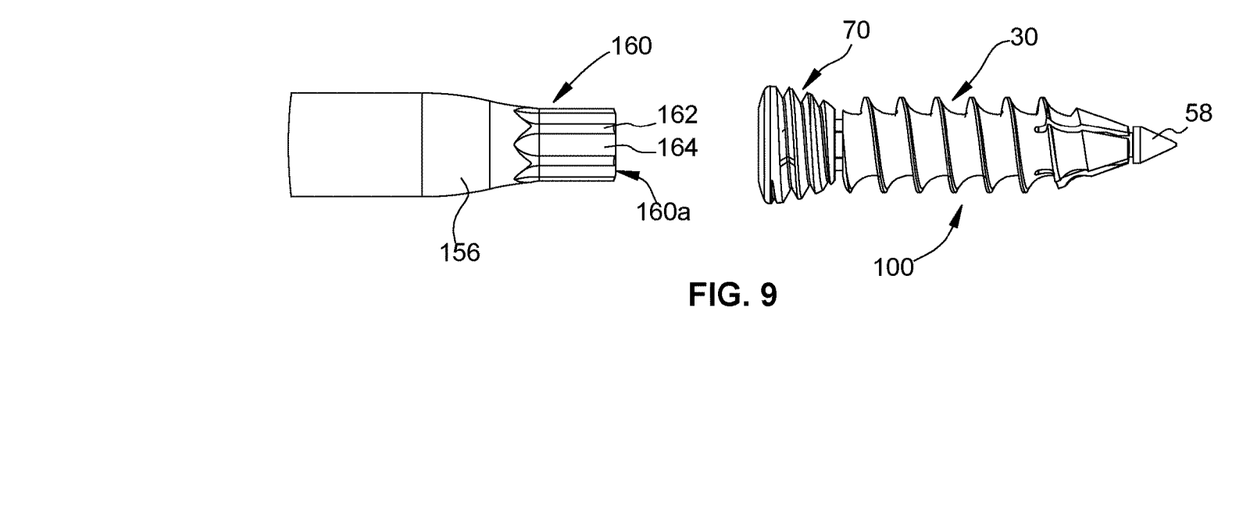
FIG. 9 is an enlarged view of the indicated area of detail delineated in FIG. 8.
Figure 10:
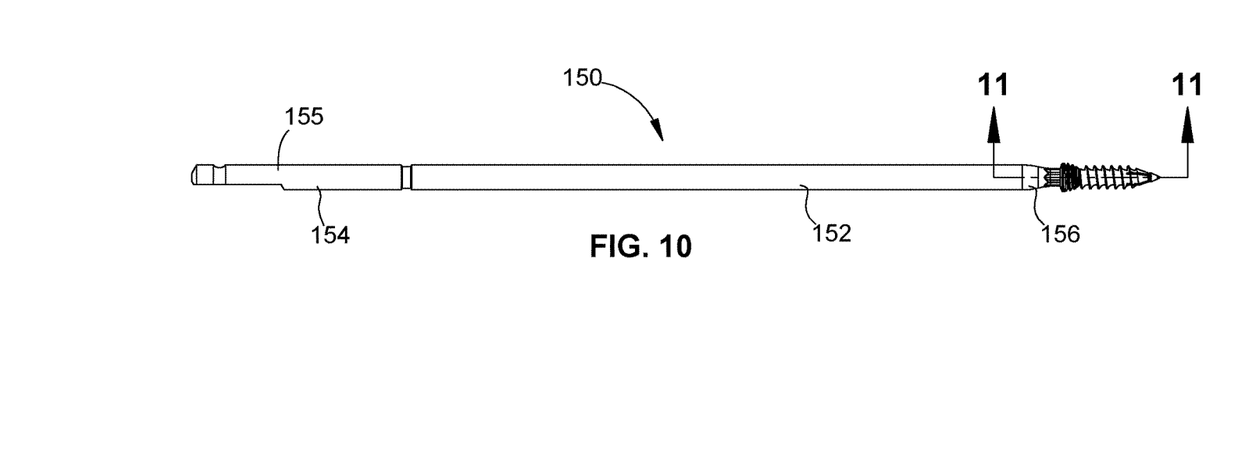
FIG. 10 is a side view of the driving tool and semi-constrained bone screw of FIG. 8 with the semi-constrained bone screw coupled to the driving tool.

Referring now to FIGS. 5-7, the angulation of the head 70 relative to the tubular body 30 and the shaft 50 is illustrated. The head 70 is repositionable at an angle "α" with respect to the longitudinal axis of the shaft 50 such that the distal surface 78 of the head 70 abuts the proximal surface 36 of the tubular body 30. Where the distal surface 78 abuts the proximal surface 36 of the tubular body 30, the gap "G" is at a minimum while a gap at a location circumferentially opposite to this (i.e., 180 degrees) is at a maximum. The outwardly flared distal portion 76 of the lumen 72 allows for an increase in the degree of angulation over, e.g., a lumen that would have a more uniform inner diameter. The underside of the flared portion 62 of the shaft 50 allows the inwardly tapered distal region 74 of the lumen 72 to slide across its surface allowing relative angular movement between the head 70 and the shaft 50 of the bone screw 100, which is clearly illustrated in at least FIG. 6. This configuration also defines the maximum angle "α" between the head 70 and the shaft 50 of the bone screw 100. It is contemplated that the head 70 may be repositioned at an angle "α" ranging from about 0 degrees to about 15 degrees from the central longitudinal axis in either direction. As such, the head 70 has a conical range of motion up to approximately 30 degrees. In one embodiment, the head is repositionable at an angle "α" ranging from about 0 degrees to about 7 degrees from the central longitudinal axis in either direction. As such, the head 70 has a conical range of motion up to approximately 14 degrees. When the head 70 is at 0 degrees, the lumen 72 of the head 70 is coaxially aligned with the shaft 50 and the tubular body 30 (FIG. 1), while the maximum angulation "α" is illustrated in FIGS. 5 and 6. As shown in FIG. 7, even at the maximum angulation "α", the inner surface 72a of the lumen 72 is still readily accessible for receiving the driving tool 150 and also maintains secure engagement with the corresponding hexolobular flared portion 62 of the shaft 50, which promotes smooth transfer of the rotational movement of the driving tool 150 to the bone screw 100 for insertion or removal into, e.g., bone or bone plates. In embodiments, head 70 may be configured to lock at any angle "α," as desired.

The helical thread 34 on the tubular body 30 is configured for securely engaging bone. The threading 80 of the head 70 of the bone screw 100 may also engage bone, or, e.g., a spinal prosthetic device (e.g., spinal implant) and/or a bone plate. In embodiments, the pitch of helical thread 34 of tubular body 30 may be greater than the pitch of threading 80 of head 70. In other embodiments, helical thread 34 of tubular body 30 and threading 80 of head 70 may have a uniform pitch.

An example of a suitable spinal prosthetic device is disclosed in commonly owned U.S. Pat. No. 8,439,977, the entire contents of which is incorporated herein by reference. An example of a suitable bone plate is disclosed in commonly owned U.S. Pat. No. 8,449,585, the entire contents of which is incorporated herein by reference. One technique for securing the head 70 of the bone screw 100 to the spinal prosthetic or the bone plate is to form the head 70 from a material having a hardness greater than a hardness of the spinal prosthetic or bone plate. This may be accomplished by forming the head 70 from a titanium alloy such as Ti-6Al-4V, and forming the spinal prosthetic or bone plate from commercially pure titanium. As the head 70 rotates and engages the softer commercially pure titanium, it deforms the commercially pure titanium, providing secure engagement between the head 70 and the bone plate and inhibiting the head 70 from backing out or separating from the spinal prosthetic or bone plate. Due to the difference in material hardness between the bone screw 100 and the bone plate, the bone screw 100 may engage and deform the bone plate through a reshaping process, which creates an autogenic lock between the bone screw 100 and the bone plate upon insertion of the bone screw 100 into the bone plate.

As used in a spinal construct, the bone plate spans adjacent vertebrae and bone screws 100 are inserted through apertures in the bone plate to secure the bone plate to the vertebrae. As the heads 70 of the bone screw(s) 100 are secured to the bone plate, the shafts 50 and the corresponding tubular bodies of the bone screw(s) 100 have a degree of angulation "α" that accommodates relative movement of the adjacent vertebrae without negatively impacting the bone screws' 100 securement to the bone plate. Thus, the bone screws 100 are secured to the bone plate and the bone plate retains a degree of movement relative to the vertebrae due to the semi-constrained features of the bone screw(s) 100.

Referring now to FIGS. 8-11, in use, bone screws 100 are inserted into a spinal prosthetic or bone plate using driving tool 150. Driving tool 150 has an elongate shaft 152 having a proximal portion 154 and an opposed distal portion 156. The proximal portion 154 of the elongate shaft 152 defines a handle 155 that is configured to enable, e.g., a clinician, to selectively rotate the driving tool 150, e.g., by gripping the handle 155 and applying a rotational force thereto. Additionally or alternatively, another instrument such as a handle (not shown) may be inserted over, and engaged with, the proximal portion 154 to rotate the driving tool 150 therewith.

The distal portion 156 of the driving tool 150 tapers to a driving bit or a reduced diameter engagement region 160. The engagement region 160 includes protrusions 162 and recesses 164 that are complementary to the inner surface 72a of the lumen 72 (FIG. 3). Once the engagement region 160 is inserted into the lumen 72, rotation of driving tool 150 results in rotation of bone screw 100 via head 70. Thus, driving tool 150 is capable of rotating bone screw 100 for insertion or removal from bone. Further still, the engagement region 160 includes a cavity or chamber 166 (FIG. 11) that is configured and dimensioned to releasably engage fingers 66 of the shaft 50. Inserting the engagement region 160 into lumen 72 positions the chamber 166 in proximity to fingers 66 of the shaft 50.

Figure 11:
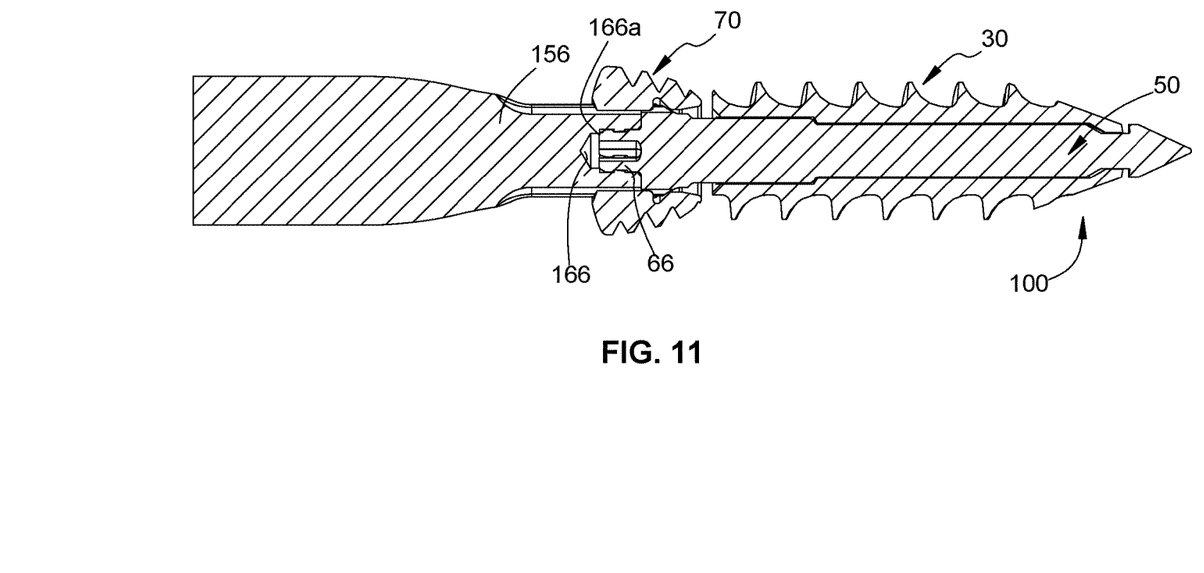
FIG. 11 is a side cross-sectional view taken along section line 11-11.

Continued advancement of the driving tool 150 results in a camming action between an inner surface of chamber 166 and outer surfaces of fingers 66 of the shaft 50. As a result, fingers 66 flex inwardly into a compressed position towards the central longitudinal axis of the shaft 50 allowing engagement region 160 to be fully seated in lumen 72 such that a distal end surface 160a of the engagement region 160 is substantially flush with the top surface 62b of flared portion 62 of the shaft 50. Simultaneously, proximal portions of fingers 66 are aligned with a groove 166a in chamber 166 that allows the fingers 66 to move towards their initial positions. The engagement between the proximal portions of fingers 66 and the groove 166a in chamber 166 releasably couples the driving tool 150 to the bone screw 100.

As the head 70 of bone screw 100 is pivotable, e.g., (repositionable at angle "α") with respect to the shaft 50 and/or the tubular body 30 of the bone screw 100, driving tool 150 is capable of driving the bone screw 100 into or out of bone even as a central longitudinal axis of the driving tool 150 is not coaxially aligned with the central longitudinal axis of the bone screw 100. Thus, as the bone screw 100 is driven into, e.g., a bone or bone plate, the head 70 may remain pivotable while the proximal region of bone screw 100 (e.g., tubular body 30) is constrained within the bone or bone plate. As head 70 is driven to its distal most position within the bone and bone plate, the threading 80 of head 70 may engage an aperture of the bone plate to resist backing out of the bone screw 100 from the bone or bone plate. In embodiments, a torque of 20 in-lbs may be applied to each bone screw 100 for sufficient affixation to, e.g., the bone or bone plate. Once the procedure is completed, the driving tool 150 is separable from the bone screw 100 by moving the driving tool 150 proximally with respect to the bone screw 100.

It will be understood that various modifications may be made to the embodiments of the presently disclosed bone screw. The aforementioned principles are applicable to any implant using a bone screw for fastening the implant to bone. Therefore, the above description should not be construed as limiting, but merely as exemplifications of embodiments. Those skilled in the art will envision other modifications within the scope and spirit of the present disclosure.

What is claimed is:

1. A bone screw comprising:
 a tubular body defining a first longitudinal axis and having open proximal and distal ends defining a passageway therethrough;
 a helical thread circumscribing an outer surface of the tubular body;
 a head having a lumen extending therethrough, wherein a proximal opening of the lumen has a diameter greater than a diameter of a distal opening of the lumen, and a portion of an interior surface of the lumen tapers inwardly toward the distal opening of the lumen; and
 a shaft slidably insertable through the lumen of the head and the passageway of the tubular body and into engagement therewith to rotatably fix the shaft relative to the tubular body, wherein a distal portion of the shaft is disposed distal of the distal end of the tubular body, wherein a proximal portion of the shaft is flared outwardly and has a maximum diameter greater than a maximum diameter of the distal portion of the shaft and greater than the diameter of the distal opening of the lumen of the head, and a portion of an exterior surface of the shaft tapers inwardly toward the distal portion of the shaft and is configured to at least partially contact the tapered interior surface of the lumen of the head when the shaft is assembled to the head, the shaft defining a second longitudinal axis, wherein the shaft couples the head to the tubular body such that a gap is defined between a distal surface of the head and the open proximal end of the tubular body, the head repositionable with respect to the first longitudinal axis of the tubular body and the second longitudinal axis of the shaft, wherein the shaft is configured to rotatably couple the tubular body to the head such that rotation of the head effectuates a corresponding rotation of the tubular body.

2. The bone screw of claim 1, wherein the head is configured to define an acute angle with respect to the second longitudinal axis of the shaft.

3. The bone screw of claim 1, wherein the passageway of the tubular body defines a proximal cavity having a first diameter and a distal cavity having a second diameter less than the first diameter.

4. The bone screw of claim 3, wherein the shaft has a proximal body portion and a distal body portion, the proximal body portion configured for insertion into the proximal cavity of the tubular body and the distal body portion configured for insertion into the distal cavity of the tubular body.

5. The bone screw of claim 4, wherein the proximal body portion of the shaft includes a hexagonal configuration that is complementary to a hexagonal configuration of the proximal cavity of the tubular body thereby inhibiting relative rotation between the shaft and the tubular body.

6. The bone screw of claim 4, wherein the shaft includes a neck portion distal of the distal body portion and a tip located distally of the neck portion, the open distal end of the tubular body sized to receive the neck portion.

7. The bone screw of claim 6, wherein the tip is pointed for engaging bone.

8. The bone screw of claim 6, wherein the neck portion of the shaft has an outer diameter less than an outer diameter of the distal body portion and the tip of the shaft such that the neck portion is retained in a channel of the open distal end of the tubular body thereby inhibiting relative axial movement between the shaft and the tubular body.

9. The bone screw of claim 1, wherein the lumen of the head is configured for releasably engaging a driving tool.

10. The bone screw of claim 9, wherein a distal portion of the driving tool is attachable to fingers of the flared portion of the shaft.

11. The bone screw of claim 1, wherein a portion of an interior surface of the lumen of the head at the distal opening tapers outwardly to increase an angular range of the head relative to the shaft.

12. The bone screw of claim 1, wherein a distal region of the tubular body includes one or more slits extending proximally from the open distal end such that the distal region of the tubular body is expandable to allow the shaft to be inserted through the open distal end.

13. A system for securing spinal fixation devices, the system comprising:
 the bone screw of claim 1; and
 a driving tool including:
  an elongate shaft having a proximal portion and a distal portion;
  a handle extending from the proximal portion of the elongate shaft;
  a driving bit extending from the distal portion of the elongate shaft, the driving bit having a hexagonal configuration on an outer surface thereof, the driving bit defining a cavity therein.

14. The system of claim 13, wherein the driving bit has a diameter that is less than a diameter of the elongate shaft.

15. The system of claim 13, wherein the hexagonal configuration of the driving bit is complementary to a hexagonal configuration of the lumen of the head of the bone screw to enable selective rotation of the bone screw.

16. The system of claim 14, wherein the flared proximal portion of the shaft of the bone screw includes fingers that are selectively attachable with the cavity of the driving bit.

17. The system of claim 16, wherein the cavity of the driving bit defines a groove therein, the fingers of the flared portion being selectively receivable in the groove to axially fix the bone screw to the driving tool.

18. A method of performing a spinal procedure, comprising:
 attaching the bone screw of claim 1 to a driving tool;
 rotating the driving tool; and
 fastening the bone screw into a bony structure.

19. The method of claim 18, wherein attaching the bone screw to the driving tool includes the driving tool with an elongate shaft having a proximal portion and a distal portion and a driving bit extending from the distal portion of the elongate shaft, the driving bit having a hexagonal configuration on an outer surface thereof and defining a cavity therein.

20. The method of claim 19, further comprising:
 positioning the head of the bone screw to define an acute angle with respect to the second longitudinal axis of the shaft of the bone screw.

21. The method of claim 18, further comprising:
 inserting fingers of the flared proximal portion of the shaft into a groove defined in the cavity of the driving bit; and
 advancing the driving tool distally until the fingers are selectively and releasably coupled in the groove to axially fix the bone screw to the driving tool.

22. A bone screw comprising:
 a tubular body defining a first longitudinal axis and having open proximal and distal ends defining a passageway therethrough;

a helical thread circumscribing an outer surface of the tubular body;

a head having a lumen extending therethrough; and a shaft slidably insertable through the lumen of the head and the passageway of the tubular body and into engagement therewith to rotatably fix the shaft relative to the tubular body, wherein a portion of the shaft is disposed distal of the distal end of the tubular body, the shaft defining a second longitudinal axis, wherein the shaft couples the head to the tubular body such that a gap is defined between a distal surface of the head and the open proximal end of the tubular body, the head repositionable with respect to the first longitudinal axis of the tubular body and the second longitudinal axis of the shaft, wherein the shaft is configured to rotatably couple the tubular body to the head such that rotation of the head effectuates a corresponding rotation of the tubular body, wherein the passageway of the tubular body defines a proximal cavity having a first diameter and a distal cavity having a second diameter less than the first diameter, wherein the shaft has a proximal body portion and a distal body portion, the proximal body portion configured for insertion into the proximal cavity of the tubular body and the distal body portion configured for insertion into the distal cavity of the tubular body, wherein the shaft includes a neck portion distal of the distal body portion and a tip located distally of the neck portion, the open distal end of the tubular body sized to receive the neck portion, wherein the neck portion of the shaft has an outer diameter less than a minimum outer diameter of the distal body portion and an outer diameter of the tip of the shaft such that the neck portion is retained in a channel of the open distal end of the tubular body thereby inhibiting relative axial movement between the shaft and the tubular body.

* * * * *